United States Patent [19]  [11] 4,091,089
Chichibu et al.  [45] May 23, 1978

[54] METHOD FOR QUANTITATIVE DETERMINATION OF AN ANTIGENIC SUBSTANCE

[75] Inventors: Kenji Chichibu, Niiza; Kiyoshige Wakabayashi, Ohmiya, both of Japan

[73] Assignee: Chugai Seiyaku Kabushiki Kaisha, Tokyo, Japan

[21] Appl. No.: 672,497

[22] Filed: Mar. 31, 1976

[30] Foreign Application Priority Data

Apr. 10, 1975  Japan ................................. 50-42803

[51] Int. Cl.$^2$ ..................... G01N 21/02; G01N 31/02; G01N 33/16
[52] U.S. Cl. ................................. 424/12; 23/230 B; 424/8; 424/11; 424/13
[58] Field of Search ........................ 424/8, 11, 12, 13; 23/230 B

[56] References Cited

U.S. PATENT DOCUMENTS 3,284,434  11/1966  Sutherland ...................... 424/12 X
3,901,654  8/1975  Gross .................................. 424/1

OTHER PUBLICATIONS

Kabat, Exptl. Immunochem, C. C. Thomas Puk Springfield, Ill., 2nd ed. 1961 pp. 22-33, 39-41, 46-47, 51-54, 69-72.

*Primary Examiner*—Albert T. Meyers
*Assistant Examiner*—A. P. Fagelson
*Attorney, Agent, or Firm*—Browdy and Neimark

[57] ABSTRACT

A method for the quantitative determination of antigenic substance without any confirmation test which comprises adding to a sample to be assayed an exogenous antigenic substance in a certain amount, combining the resulting mixture with an antibody specific to the antigenic substance to cause antigen-antibody reaction and measuring the amount of the precipitates formed, and a diagnostic kit for practicing the method are disclosed.

2 Claims, 8 Drawing Figures

METHOD FOR QUANTITATIVE DETERMINATION OF AN ANTIGENIC SUBSTANCE

This invention relates to a method of quantitative determination of an antigenic substance and a diagnostic kit to practice the method.

In the clinical diagnostic field, determination of the amount of an antigenic substance, for example, immunoglobulin, albumin, $\alpha_1$-antitrypsin, transferrin, heptoglobin and complement components, has been generally adopted for the purpose of diagnosis and for reference in treatment of various diseases.

Single diffusion in a plate or in a tube are well known methods for quantitative determination of these substances. The single diffusion in a plate method is usually carried out by preparing a support plate of an agar gel containing an antibody specific to an antigenic substance (antigen) to be assayed, placing the antigenic substance into a small hole formed in the gel plate, allowing the plate to stand at a predetermined temperature for a certain period of time to allow the antigenic substance to diffuse through the gel plate and to react with the antibody and measuring the size of the ring of white precipitates (reaction product) formed around the hole.

On the other hand, single diffusion in a tube is carried out by putting an antigenic substance on an antibody containing agar gel in a glass tube wherein the antigen reacts with the antibody. In this method, the antigen diffuses in the gel from the top toward the bottom forming a sharp band of precipitates, reaction products, and the movement of the band terminates at the point where the system reaches its equilibrium state. The amount of the antigen is determined by measuring the distance between the top of the gel and the band finally stopped.

These methods, however, are advantageous because it takes a long time, i.e. 1 - 2 days usually, for diffusion and completion of the reaction and a further 1 - 2 days when a sample happens to contain the antigen in an amount over the properly measurable range. Further, it is not easy with these methods to obtain accurate values since the determination is made by visual observation through a magnifying glass.

A turbidimetric method is also known in addition to the methods mentioned above using agar plate or tube. This method utilizes correlation between the amounts of an antigen and precipitates and is based on the fact that the curve as shown in FIG. 1 can be obtained in the precipitation reaction between an antigen and an antibody when the amount of antibody is constant. Although the amount of the antigen can be determined by measuring turbidity of the reaction mixture according to this method, it is necessary to confirm which is the real amount, X in the antigen-shortage region and Y in the antigen-surplus region, since a value of turbidity provides two values for the antigen, X and Y. This test is referred to as a "confirmation test" in this specification. Because of this fact, this method cannot be said to suitable for testing of a large number of samples within a limited time.

The present method has been established to overcome the defects in the foregoing methods. Namely, it becomes possible with this invention to easily and correctly determine the amount of an antigenic substance without the confirmation test.

This invention comprises adding the exogenous antigenic substance, which was separately prepared and is identical to the antigenic substance to be assayed, to a test sample in an amount sufficient to give the maximum precipitation by the reaction with the antibody to be used or in an amount slightly in excess of such amount, combining the resulting mixture with an antibody specific to the antigenic substance to cause antigen-antibody reaction, and measuring turbidimetrically the amount of precipitates formed.

According to the invention, the amount of an antigenic substance is determined by only using the curve in the antigenic substance-surplus region, i.e. the latter half of the standard curve shown in FIG. 1 starting from the point Z. Thus, it is unnecessary to do a "confirmation test".

According to this invention, the method is practiced as follows: An antibody and a sample containing an antigenic substance are separately diluted with a buffer solution, e.g. phosphate buffer saline solution, Tris-HCl buffer saline solution or veronal buffer saline solution, to a level each suitable for antigen-antibody reaction and for subsequent measurement of turbidity of the sample. The exogenous antigenic substance separately prepared is also diluted with the same buffer solution to a level at which it can be easily measured and will give the maximum precipitation. To a diluted antigenic substance is added a diluted exogenous antigenic substance and the mixture is further mixed with a diluted antibody to cause antigen-antibody reaction at a temperature of from 10° - 40° C, preferably 20° - 37° C for a predetermined time. The amount of the antigenic substance can be determined by turbidimetrically measuring the amount of the precipitates and comparing with the standard curve which was previously prepared by using the same antibody and standard antigen solutions of various known concentrations.

This method is applicable to all kinds of antigenic substances, for example, immunoglobulins such as IgG, IgA and IgM, albumin, $\alpha_1$-antitrypsin, transferrin, heptoglobin and complement components such as complement component $C_3$.

According to the method of this invention, an antigenic substance can be quantitatively determined easily and correctly in a short period of time. Further, the method can be formulated, for practical use, into a diagnostic kit consisting of (a) a buffer solution to dilute a sample to be determined, (b) an exogenous antigenic substance separately prepared in an amount sufficient to give the maximum precipitation by the reaction with the antibody used, (c) an antibody solution which is diluted to a concentration suitable for the antigen-antibody reaction and (d) a series of standard antigenic substance solutions, each containing a different known amount of an antigenic substance.

The present invention is further illustrated by the following examples, but they are not to be construed as limiting the scope of this invention.

EXAMPLE 1

Figure 1:
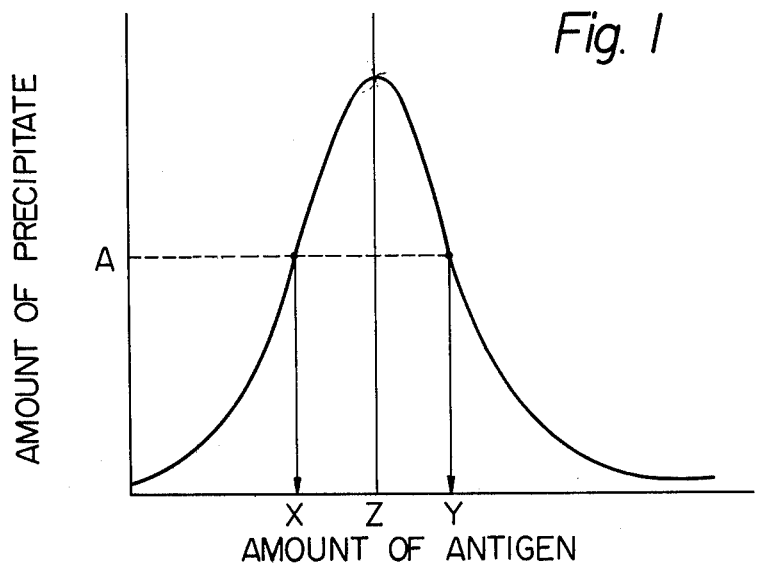
FIG. 1 is a graph showing the correlation between the amounts of antigenic substance to be assayed and precipitates formed by the conventional turbidimetric method when the concentration of the antibody to be reacted with the antigenic substance is constant.
Figure 2:
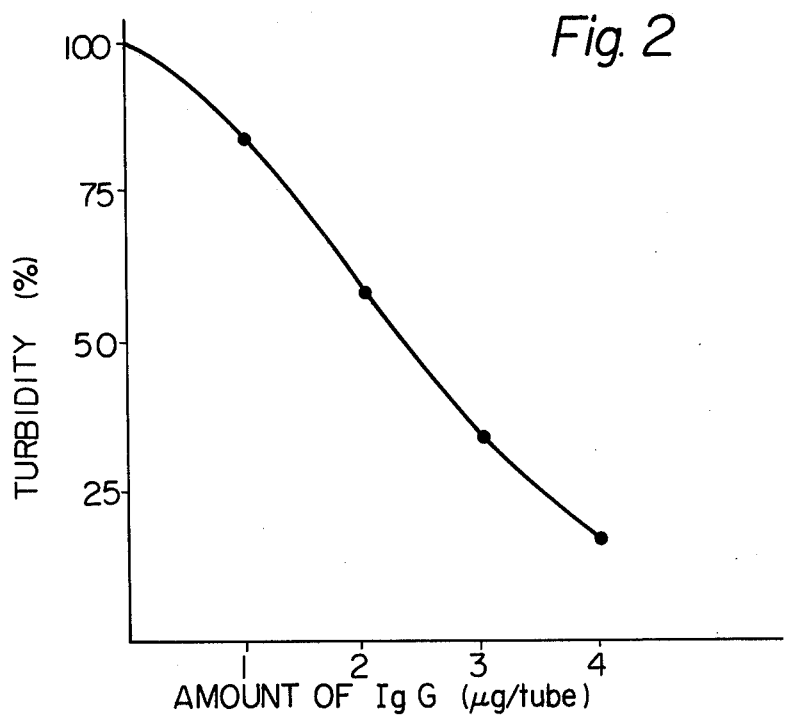
FIGS. 2-8 are graphs showing the standard curves for assaying IgG, IgA, IgM, complement component $C_3$, heptoglobin, transferrin and $\alpha_1$-antitrypsin, respectively.

A diluted serum (0.95 ml) containing 11 μg of IgG (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of IgG and the anti-serum (antibody) diluted 60 times by volume with a 0.001 M phosphate buffer saline solution (pH: 7.4; 1.0 ml) were added to each tube to make the volume of mixture 2 ml in each tube. Each mixture was kept at 37° C for 30 minutes and then its turbidity was measured by a turbidimeter. The correlation between the antigenic substance IgG assayed and the precipitates formed is shown in FIG. 2.

EXAMPLE 2

To 0.1 ml, each of 30 samples of human serum, diluted 80 times with phosphate buffer saline solution (pH 7.4), each in a separate tube was added 0.9 ml (corresponding to 110 μg) of IgG (exogenous antigenic substance) and mixed thoroughly. The mixture (0.1 ml) was taken out of each tube and 1.0 ml of the antibody diluted 60 times with the same buffer solution and 0.9 ml of the phosphate buffer saline solution (pH 7.4) were added to the mixture to allow it to cause antigen-antibody reaction at 26° C. After 30 minutes passed, turbidity was determined by a turbidimeter and the results were compared with the graph obtained in Example 1 to obtain the value of 1,307 mg/dl as the mean value of 30 samples, which corresponds to the normal value of a healthy person.

A recovery test was carried out using a sample optionally taken out of 30 samples of the human serum by adding a known amount of IgG to the sample. The results are shown in the Table.

Table

| IgG added (mg/dl) | Calculated (mg/dl) | Found (mg/dl) | Recovery Rate* (%) |
|---|---|---|---|
| 0 | — | 2,160 | — |
| 525 | 2,685 | 2,800 | 104 |
| 1,050 | 3,210 | 3,280 | 102 |
| 2,100 | 4,260 | 4,200 | 99 |

*Recovery Rate(%) = $\frac{\text{Found}}{\text{Calculated}} \times 100$

EXAMPLE 3

Figure 3:
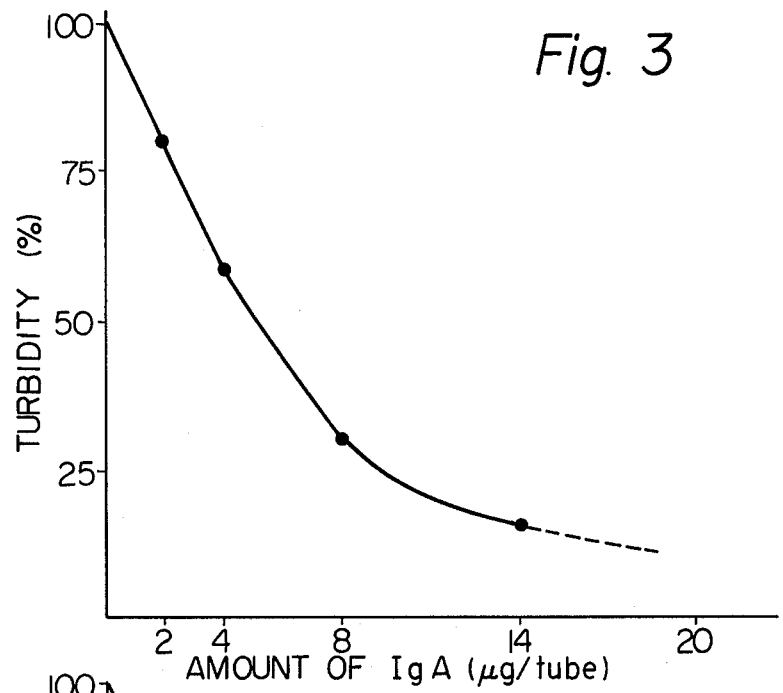

A diluted serum (0.95 ml) containing 17 μg of IgA (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of IgA and the anti-serum (antibody) diluted 20 times by volume with a 0.001 M-phosphate buffer saline solution (1.0 ml: pH, 7.4) were added to each tube to make the volume of mixture 2.0 ml. Each mixture was kept at 37° C for one hour and then its turbidity was measured by a turbidimeter. The correlation between the antigenic substance IgA assayed and the precipitates formed is shown in FIG. 3.

The recovery test was carried out in the same manner as in Example 2 to give satisfactory results.

EXAMPLE 4

Figure 4:
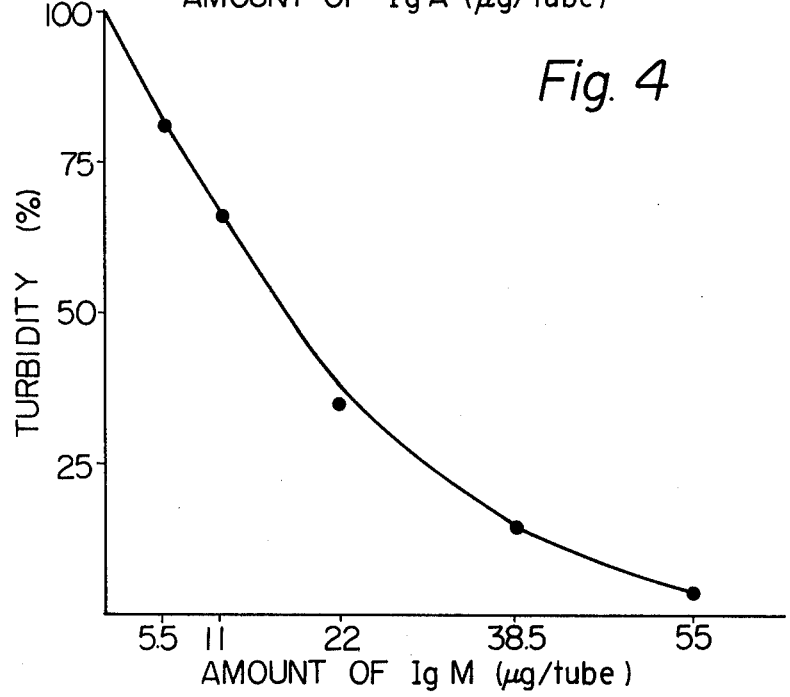

A diluted serum (0.95 ml) containing 25 μg of IgM (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of IgM and the anti-serum (antibody) diluted 30 times by volume with a 0.001 M-veronal buffer saline solution (1.0 ml: pH, 7.4) were added to each tube to make the volume of mixture 2.0 ml. Each mixture was kept at 37° C for one hour and then its turbidity was measured by a turbidimeter. The correlation between the antigenic substance IgM assayed and the precipitates formed is shown in FIG. 4.

The recovery test was carried out in the same manner as in Example 2 to give satisfactory results.

EXAMPLE 5

Figure 5:
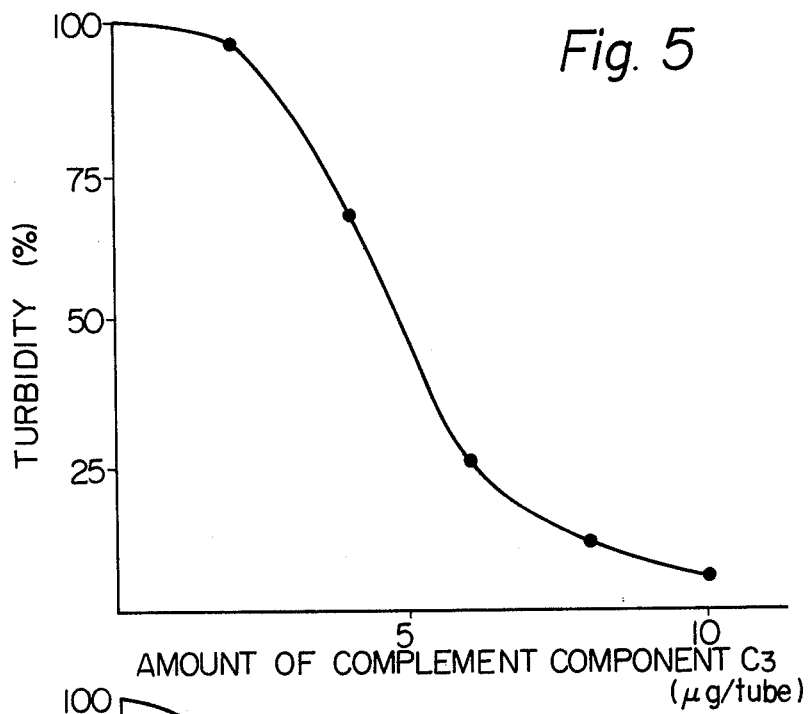

A diluted serum (0.95 ml) containing 18 μg of complement component $C_3$ (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of complement component $C_3$ and the anti-serum (antibody) diluted 20 times by volume with a 0.001 M-phosphate buffer saline solution (1.0 ml: pH, 7.4) were added to each tube to make the volume of mixture 2.0 ml. Each mixture was kept at 37° C for one hour and then its turbidity was measured by a turbidimeter. The correlation between the antigenic substance complement component $C_3$ assayed and the precipitates formed is shown in FIG. 5.

The recovery test was carried out in the same manner as in Example 2 to give satisfactory results.

EXAMPLE 6

Figure 6:
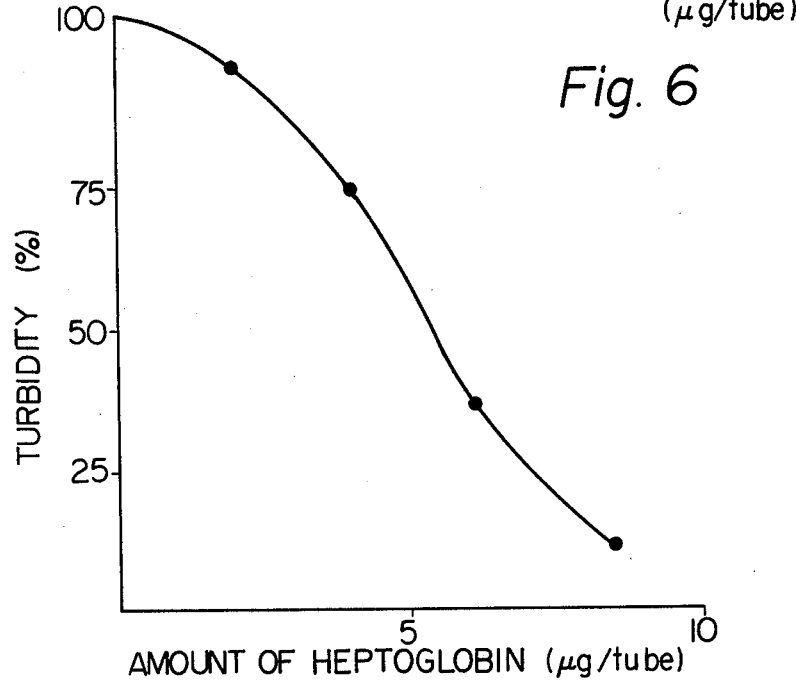

A diluted serum (0.95 ml) containing 15 μg of heptoglobin (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of heptoglobin and the anti-serum (antibody) diluted 20 times by volume with a 0.001 M-phosphate buffer saline solution (1.0 ml: pH, 7.4) were added to each tube to make the volume of mixture 2.0 ml. Each mixture was kept at 37° C for one hour and then its turbidity was measured by a turbidimeter. The correlation between the antigenic substance heptoglobin assayed and the precipitates formed is shown in FIG. 6.

The recovery test was carried out in the same manner as in Example 2 to give satisfactory results.

EXAMPLE 7

Figure 7:
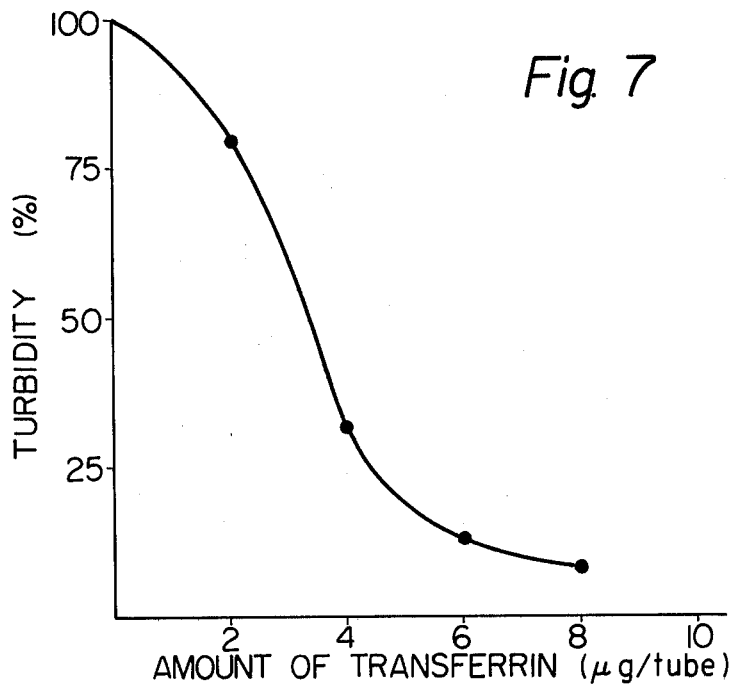

A diluted serum (0.95 ml) containing 14 μg of transferrin (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of transferrin and the anti-serum (antibody) diluted 60 times by volume with a 0.001 M-phosphate buffer saline solution (1.0 ml:

pH, 7.4) were added to each tube to make the volume of mixture 2.0 ml. Each mixture was kept at 37° C for one hour and then its turbidity was measured by a turbidimeter. The correlation between the antigenic substance transferrin assayed and the precipitates formed is shown in FIG. 7.

The recovery test was carried out in the same manner as in Example 2 to give satisfactory results.

EXAMPLE 8

To 0.1 ml, each of 30 samples of human serum diluted 20 times with 0.001 M-phosphate buffer saline solution (pH 7.4) each in a separate tube was added 1.0 ml (corresponds to 14 μg) of transfer in (exogenous antigenic substance) and they were mixed well. The antibody (1.0 ml) diluted 60 times with the same buffer solution was added to the mixture to allow it to cause antigen-antibody reaction at 37° C. After 60 minutes passed, its turbidity was determined by a turbidimeter and the results were compared with the graph obtained in Example 7 to obtain the value 291 mg/dl as the mean value of the 30 samples, which corresponds to the normal value of a healthy person.

A recovery test was carried out as in Example 2 using a sample optionally taken out of 30 samples of the human serum to give good results.

EXAMPLE 9

Figure 8:
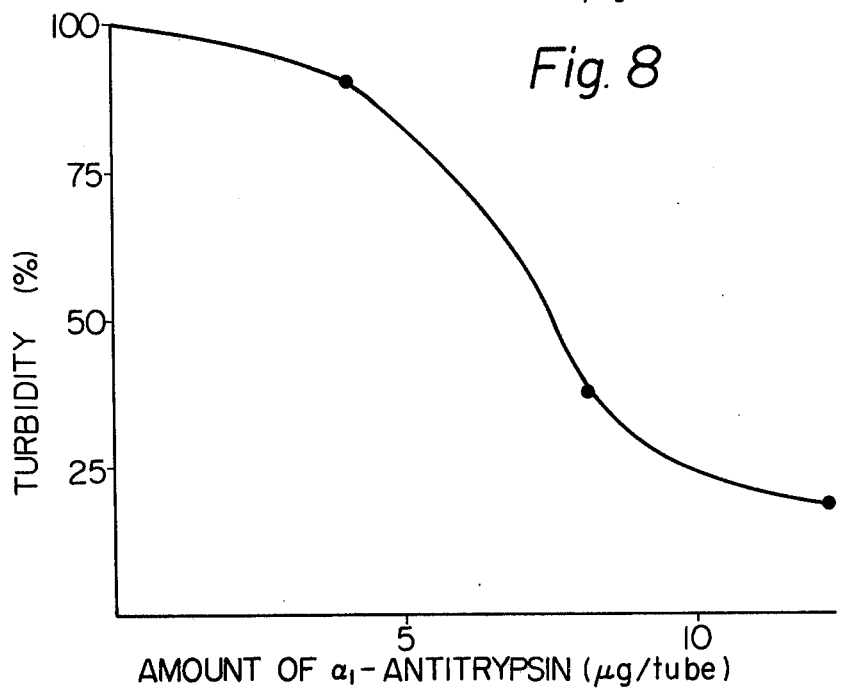

A diluted serum (0.95 ml) containing 28 μg of $\alpha_1$-antitrypsin (exogenous antigenic substance) the amount of which is such that it gives the maximum amount of precipitates by the reaction with the antibody used was placed in each of the tubes employed in this test. The standard serum (standard antigenic substance) (0.05 ml) containing a different known amount of $\alpha_1$-antitrypsin and the antiserum (antibody) diluted 20 times by volume with a 0.001 M-veronal buffer saline solution (1.0 ml: pH, 7.4) were added to each tube to make the volume of mixture 2.0 ml. Each mixture was kept at 37° C for one hour and then its turbidity was measured by a turbidimeter. The correlation between the antigenic substance $\alpha_1$-antitrypsin assayed and the precipitates formed is shown in FIG. 8.

The recovery test was carried out in the same manner as in Example 2 to give satisfactory results.

EXAMPLE 10

Preparation of a diagnostic kit for the quantitative determination of IgG

The diagnostic kit was prepared as follows:

(a) A buffer solution tube; 0.99 ml of 0.001 M veronal buffer saline solution (pH, 7.4), (b) An exogenous IgG tube; 0.98 ml of anti-serum containing 11 μg of IgG the amount of which is such that it gives the maximum amount of precipitates by the reaction with the antibody used, (c) An antibody bottle; anti-serum diluted with 0.001 M veronal buffer solution (pH, 7.4) to a level suitable for antigen-antibody reaction, and (d) A series of standard IgG solutions; each serum containing a different known amount of IgG, 2, 4, 6, 8 and 10 μg/0.02 ml of serum.

This diagnostic kit can be used as follows:

The sample (0.01 ml) is put in the buffer solution tube (a) and they are mixed well, and 0.02 ml of the mixture is carried into the tube of exogenous IgG (b). One ml of the antibody is taken out of the bottle of antibody (c) and put into the tube of the mixture to allow antigen-antibody reaction at 37° C for 60 minutes, followed by determining turbidity using turbidimeter.

Meanwhile, the same procedure is used with the standard buffer solution instead of sample to obtain a standard curve, and the amount of IgG is determined by comparison with this standard curve.

What we claim is:

1. A method for the quantitative determination of antigenic substance which comprises adding to a sample the same exogenous antigenic substance as that to be assayed, separately prepared, in such an amount as to give the maximum precipitation by the reaction with the antibody used, combining the resulting mixtures with an antibody specific to the antigenic substance to be assayed to cause antigen-antibody reaction, and measuring turbidimetrically the amount of precipitates formed by the reaction, whereby the amount of precipitate will always be on the antigen-surplus side of the precipitate versus antigen curve formed for any given amount of antibody.

2. A method for the quantitative determination of an antigenic substance according to claim 1 in which the antigenic substance is selected from the group consisting of immunoglobulin G, immunoglobulin A, immunoglobulin M, albumin, $\alpha_1$-antitrypsin, transferrin, heptoglobin and complement components.

* * * * *

UNITED STATES PATENT AND TRADEMARK OFFICE
CERTIFICATE OF CORRECTION

PATENT NO. : 4,091,089
DATED : May 23, 1978
INVENTOR(S) : CHICHIBU et al

It is certified that error appears in the above-identified patent and that said Letters Patent are hereby corrected as shown below:

Column 1, line 39, cancel "advantageous" and insert
--disadvantageous--

Column 5, line 16, cancel "transfer in" and insert
--transferrin--

Signed and Sealed this

Fifteenth Day of May 1979

[SEAL]

Attest:

RUTH C. MASON
Attesting Officer

DONALD W. BANNER
Commissioner of Patents and Trademarks